United States Patent [19]

Decker et al.

[11] 4,230,683
[45] Oct. 28, 1980

[54] HAPTEN CONJUGATED ANTIBODY FOR ANTIBODY OR ANTIGEN DETECTION

[75] Inventors: Richard H. Decker, Deerfield; Chung-Mei Ling, Antioch; Lacy R. Overby, Lake Forest, all of Ill.

[73] Assignee: Abbott Laboratories, North Chicago, Ill.

[21] Appl. No.: 932,394

[22] Filed: Aug. 9, 1978

[51] Int. Cl.$^2$ .................... G01N 33/16; A61K 39/00; A61K 43/00
[52] U.S. Cl. .................................... 424/1; 23/230 B; 424/12
[58] Field of Search .................... 424/1, 12; 23/230 B

[56] References Cited

U.S. PATENT DOCUMENTS

| 4,012,494 | 3/1977 | Ling | 424/1 |
| 4,034,072 | 7/1977 | Mjos et al. | 424/1 |

Primary Examiner—Benjamin R. Padgett
Assistant Examiner—Christine M. Nucker
Attorney, Agent, or Firm—John J. McDonnell

[57] ABSTRACT

The present invention encompasses an improved method for detecting antigen or antibody bound to a solid support which involves the reaction of hapten-labeled antibody to the antigen or antibody to be detected followed by reaction of the hapten moiety with labeled antibody to the hapten and the determination of the amount of label bound to the solid support.

5 Claims, No Drawings

HAPTEN CONJUGATED ANTIBODY FOR ANTIBODY OR ANTIGEN DETECTION

BACKGROUND OF THE INVENTION

Methods for directly binding antigens or antibodies to be detected to a solid support are well known. Also known are methods of indirectly binding an antigen or antibody to be detected to a solid support by first coating the solid support with the binding partner of the species to be detected. Generally, the solid support having the antigen or antibody to be detected bound thereto is further reacted with labeled (radioactive, enzyme, fluorescent, stable-free radical, etc.) binding partner of the antigen or antibody bound to the solid support and the amount of label bound to the solid support is determined.

Haptens are protein free bodies, generally of low molecular weight that do not induce antibody formation when injected into an animal, but are reactive to antibodies.

Antibodies to hapten are raised by first conjugating the hapten to a protein and injecting the conjugated product into an animal or human. The resulting antibodies are isolated by conventional antibody isolation techniques. Examples of haptens are steroids such as esterone, estradiol, testosterone and progesterone. Vitamins such as vitamin B-12 and folic acid, thyroxine, thyrodothyroxine, histamine, serotonis, digoxin, prostaglandin, adrenalin, noradenalin, kinetin, gibberellic acid and 2,4-dinitrophenol are suitable hapten molecules.

The 2,4-dinitrophenyl (DNP) moiety is particularly useful hapten antigenic site. This group is conveniently introduced by reacting 2,4-dinitrophenol, 2,4-dinitroaniline, or $\epsilon$-DNP-L-lysine with the antibody for the antibody or antigen to be detected.

Those skilled in the immunoassay arts will recognize a wide variety of methods for binding antibodies or antigens to solid supports; U.S. Pat. Nos. 3,939,350; 3,853,987; 3,654,090; 3,646,346 and 3,867,517. Techniques for labeling antibodies with iodine-125 ($^{125}$I) or other radioactive labels are well known: Greenwood, Hunter and Glover, Biochem. J., 89:114, (1963).

Techniques for fluorescently labeling antibodies are also well known: Feltkamp, Immunology 18, 875 (1970) and U.S. Pat. No. 3,789,116.

Likewise, enzymes such as catalase, peroxidase $\beta$-glucouronidase, glucose-6-phosphate dyhydrogenase, urease, and glucoseoxidase are conveniently linked to antibodies by art recognized techniques: U.S. Pat. Nos. 3,875,011; 3,791,932 and 3,879,262.

BRIEF DESCRIPTION OF THE INVENTION

The present invention encompasses an improvement in an immunoassay for determining antigen or antibody from a test sample bound to a solid support, the improvement comprising reacting the antigen or antibody bound to the solid support with a hapten/conjugated antibody to the antigen or antibody, further reacting hapten conjugated antibody bound to the solid support with labeled anti-hapten antibody and determining the labeled antibody bound to the solid support. This invention also encompasses antibody to hepatitis antigen having a plurality of hapten molecules bound thereto and antibody to hepatitis antibody having a plurality of hapten molecules bound thereto.

DETAILED DESCRIPTION OF THE INVENTION

The present invention encompasses an improved immunoassay method for determining antigen or antibody from a test sample bound to a solid support. The improvement comprising reacting the antigen or antibody bound to the solid support with a hapten conjugated antibody to the antigen or antibody to be detected to provide hapten conjugated antibody bound to the solid support, reacting hapten conjugated antibody bound to the solid support with labeled anti-hapten antibody, and measuring the labeled hapten antibody bound to the solid support. The invention includes hapten conjugated antibody reagents exemplified by hapten conjugated antibody to hepatitis A antigen, hapten conjugated antibody to hepatitis A antibody, hapten conjugated antibody to hepatitis B antigen, and hapten conjugated antibody to hepatitis B antibody.

Solid support refers to insoluble polymeric material sorptive for the antibody. Known materials of this type include hydrocarbon polymer such as polystyrene, polyethylene, polypropylene, polybutylene, butyl rubber and other synthetic rubbers. Other suitable organic polymers include silastic rubber, polyesters, polyamides, cellulose and cellulosic derivatives, acrylates, methacrylates, and vinyl polymers such as vinyl chloride, and polyvinyl fluoride. Copolymers such as graft copolymers of polystyrene are also useful. In addition to the foregoing materials, the solid support surface may comprise silica gel, silicone wafers, glass insoluble protein and the solid support may be in the form of beads tubes, strips disk and the like.

The method of the present invention is applicable to the determination of a wide variety of antigens and antibodies. For example, the hepatitis B surface antigen, antibody to the hepatitis B surface antigen, hepatitis A antigen, antibody to the hepatitis A antigen, hepatitis B core antigen, antibody to the hepatitis B core antigen, as well as infectious agents and their antibodies, cancer antigen and their antibodies, and tissue (organ) antigens and their antibodies.

The use of labeled antibodies ($^{125}$I, enzymes, and fluorescent chemicals) in solid phase immunoassay is well known. Indirect (sandwich) radioimmunoassay, for instance, labeled antibodies are used to detect the presence of antigens which had been previously absorbed from the test solution by solid phase-bound antibody. If the antibody is in low titer in a serum and cannot be purified, it will function poorly, if at all, at detecting the antigen. This occurs in antiserum from patients convalsecing from an infectious disease; it is not possible to boost antibody titer, and it is frequently not possible to produce high titer serum in animals.

Sometimes, one can compensate for a low titer of the detecting antibody by increasing its concentration in the reaction. However, if the antibody is tagged with $^{125}$I, a prohibitive amount of $^{125}$I must then be added.

The present invention makes use of hapten conjugated antibodies to amplify antigenicity of the bound antibody. Thus, each hapten conjugated antibody will have several hapten molecules bound thereto providing for multiplication of the antigenic reactivity.

Antigen in test sample is typically determined by reacting a solid phase coated with antibody of the antigen to be determined and further reacting the solid support with hapten conjugated antibody to the antigen to be determined followed by reaction with labeled anti-hapten antibody. In this manner, polystyrene beads having antibody to human hepatitis B surface antigen are reacted with test serum thereby binding hepatitis B surface antigen from the test sample to the polystyrene beads. The beads are then reacted with antibody to hepatitis B surface antigen having 2,4-dinitrophenyl (DNP) hapten from 2,4-dinitrophenol bound thereto. Animal (goat) antibody to the DNP moiety labeled with $^{125}I$ label bound to the bead is determined. The antigen from the test sample can be directly adsorbed on the solid support but this procedure is generally less specific.

The following examples illustrate the present invention and are not intended to limit the invention in spirit or scope.

EXAMPLE I

| Test for Hepatitis B Surface Antigen (HBsAg) | | | | |
|---|---|---|---|---|
| Solid Phase | Antibody I | Serum with Antigen | Antibody to Hapten | Anti-Hapten-$^{125}I$ |
| Polystyrene | Human anti-HBs | Serum with HBsAg | Human anti-HBs-DNP | Goat anti-DNP-$^{125}I$ | a. Preparation of antibody coated beads. 6 mm polystyrene beads are coated overnight with a solution of diluted human anti HBs (e.g., 1:200) in 0.01 M Tris, pH 9.0, 0.2 ml/bead. Beads are washed three times with 0.01 M Tris, pH 7.5 and air dried on filter paper.

b. Preparation of IgG anti HBs-DNP. IgG of human anti-HBs is prepared by precipitating γG from serum with 50% $(NH_4)_2SO_4$ for one hour and dialyzing pellet with 0.04 M phosphate, pH 7.0 overnight. IgG is isolated on DEAE cellulose by conventional fractionation. Protein eluted from DEAE with 0.04 M phosphate buffer, pH 7.5 is taken as IgG. 5 mg IgG in buffer (1 ml) is mixed with 5 mg $K_2CO_3$ and 5 mg 2,4-dinitrobenzene sulfonate and incubated overnight. The mixture is dialyzed overnight with $H_2O$ and diluted two-fold in 0.05 M borate, pH 8.0 for storage.

c. Preparation of goat anti-DNP $^{125}I$ IgG. Commercial goat anti-DNP antiserum is purified to obtain $^{125}I$ IgG. Commercial goat anti-DNP antiserum is purified to obtain IgG, as above, or is isolated by affinity chromatography by treatment of antiserum with sepharose-DNP to absorb antibody. The sepharose antibody complex is washed, and the anti-DNP is eluted from sepharose with 1.5 M acetic acid. The eluate is dialyzed with PBS to neutralize the acid, IgG or purified antibody is then iodinated with $^{125}I$ by the method of Greenwood, Hunter and Glover, Biochem. J., 89:114, (1963).

d. Assay Procedure: Test for HBsAg (Antigen)
1. Incubate antibody coated beads with 0.2 ml of test serums and positive and negative (for HBsAg) controls, 3 hours at 45° C.
2. Wash 2 times with $H_2O$ - aspiration.
3. Add 0.2 ml anti-HBs-DNP, diluted e.g., 1:10 in 50% calf serum - PBS, to each bead. Incubated 2 hours at 45° C.
4. Wash 2 times with $H_2O$ - aspiration.
5. Add anti-DNP $^{125}I$ (~200,000 cpm/0.2 ml) diluted in 50% calf serum. Incubate 1 hour at 45° C.
6. Wash 2 times with $H_2O$ - aspiration.
7. Count beads in γ counter.

An *elevation* in cpm of specimen or positive control over cpm for negative control is evidence of HBsAg.

EXAMPLE II

| Test for Antibody to HBsAg | | | | |
|---|---|---|---|---|
| Solid Phase | Antibody I | Antigen | Serum with Antibody | Antibody to Hapten Anti Hapten | Anti-Hapten $^{125}I$ |
| Polystyrene | Anti-HBs (Human) | HBsAg | Serum with anti HBs | (Human) -DNP | Goat anti-DNP-$^{125}I$ | a. Preparation of antigen-coated beads. Antibody-coated beads in Example I are incubated with a dilute solution of HBsAg in buffer (e.g., bovine serum albumin in phosphate buffer solution BSA-PBS) overnight. Beads are washed in PBS two times.

b. Preparation of anti-HBs-DNP. Same as in Example I.

c. Preparation of anti-DNP $^{125}I$. Same as in Example I.

d. Assay procedure: Test for anti-HBs:
1. Incubate HBsAg coated beads with 0.2 ml test serums, positive and negative (for anti-HBs) controls for three hours, 45° C.
2. Wash two times with $H_2O$ - aspiration.
3. Add 0.2 ml anti-HBs DNP diluted, e.g., 1:10 in 50% calf serum-PBS. Incubate 2 hours, at 45° C.
4. Wash two times with $H_2O$.
5. Add anti-DNP $^{125}I$ (~200,000 cpm per 0.2 ml) diluted in 50% calf serum. Incubate 1 hour, at 45° C.
6. Wash two times with $H_2O$ - count beads.

A *decrease* in cpm of approximately 50% (negative and positive÷2) is evidenced of anti-HBs.

What is claimed is:

1. In an immunoassay method for determining an antigen or an antibody from a test sample and bound to a solid support, the improvement comprising reacting the antigen or antibody bound to the solid support with an antibody having a hapten conjugated thereto and then reacting the hapten portion with labeled antihapten antibody, and measuring the labeled antihapten antibody bound to the solid support.

2. In an immunoassay method for determining hepatitis B surface antigen from a test sample and bound to a solid support, the improvement comprising reacting the hepatitis surface antigen bound to the solid support with an antibody to hepatitis B surface antigen, said antibody having a hapten conjugated thereto, reacting the hapten portion with labeled antihapten antibody, and measuring the labeled antihapten antibody bound to a solid support.

3. In an immunoassay method for determining hepatitis B antibody from a test sample and bound to a solid support, the improvement comprising reacting the hepatitis B antibody bound to the solid support with an antibody to the hepatitis B antibody, said antibody having a hapten conjugated thereto, reacting the hapten portion with labeled antihapten antibody, and measuring the labeled antihapten antibody bound to the solid support.

4. An immunoassay reagent which is antibody for hepatitis B surface antigen, said antibody having a hapten conjugated thereto.

5. An immunoassay reagent which is antibody to hepatitis B surface antigen, said antibody having a 2,4-dinitrophenyl moiety conjugated thereto.

* * * * *